US010932786B2

(12) United States Patent
McNamara et al.

(10) Patent No.: US 10,932,786 B2
(45) Date of Patent: Mar. 2, 2021

(54) DEVICES AND METHODS FOR TREATING PATENT DUCTUS ARTERIOSUS

(71) Applicant: Corvia Medical, Inc., Tewksbury, MA (US)

(72) Inventors: Edward I. McNamara, Chelmsford, MA (US); Matthew J. Finch, Medford, MA (US); Stephen J. Forcucci, Winchester, MA (US); Carol A. Devellian, Topsfield, MA (US)

(73) Assignee: Corvia Medical, Inc., Tewksbury, MA (US)

( * ) Notice: Subject to any disclaimer, the term of this patent is extended or adjusted under 35 U.S.C. 154(b) by 0 days.

(21) Appl. No.: 14/931,817

(22) Filed: Nov. 3, 2015

(65) Prior Publication Data

US 2016/0120550 A1    May 5, 2016

Related U.S. Application Data

(60) Provisional application No. 62/074,647, filed on Nov. 4, 2014.

(51) Int. Cl.
*A61B 17/12* (2006.01)

(52) U.S. Cl.
CPC .. *A61B 17/12109* (2013.01); *A61B 17/12172* (2013.01); *A61B 17/12036* (2013.01); *A61B 2017/1205* (2013.01)

(58) Field of Classification Search
CPC ........ A61B 17/12109; A61B 17/12036; A61B 17/12172; A61B 2017/12054;
(Continued)

(56) References Cited

U.S. PATENT DOCUMENTS

| 2006/0052821 A1* | 3/2006 | Abbott | A61B 17/0057 606/213 |
| 2008/0033478 A1* | 2/2008 | Meng | A61B 17/0057 606/194 |

(Continued)

*Primary Examiner* — Kathleen S Holwerda
*Assistant Examiner* — Brooke Labranche
(74) *Attorney, Agent, or Firm* — Helen S Liu

(57) ABSTRACT

The present teachings provide a device to close a ductus arteriosus percutaneously. One aspect of the present teachings provides a device comprising at least one flange portion configured to be positioned against a vascular wall outside one end of a ductus arteriosus, and a body portion configured to be positioned inside the ductus arteriosus. The body portion of the device has a length adjustable in order for the device to fit inside patients with various ductus arteriosus lengths. The at least one flange portion of the device has pivotability in order for at least one flange to deflect from the longitudinal axis of the body portion so that the deployed device can be positioned at a treatment site allowing the discs to sit flat against the vascular tissue to promote closure while avoiding disruption of flow within the pulmonary artery and aorta or applying excess pressure to the surrounding vascular tissue. The body portion of the device could also at least partially block the ductus arteriosus, and thereby reduce or obstruct blood flow through the ductus arteriosus. The device includes a delivery profile and a deployment profile. Another aspect of the present teachings provides methods of using a device of the present teachings.

16 Claims, 7 Drawing Sheets

(58) Field of Classification Search
CPC ........ A61B 17/12031; A61B 17/12027; A61B 17/12099; A61B 17/1214
See application file for complete search history.

(56) References Cited

U.S. PATENT DOCUMENTS

2008/0249562 A1\* 10/2008 Cahill ................ A61B 17/0057
606/215
2012/0316597 A1\* 12/2012 Fitz .................. A61B 17/12031
606/194
2013/0165967 A1\* 6/2013 Amin ................ A61B 17/0057
606/213

\* cited by examiner

DEVICES AND METHODS FOR TREATING PATENT DUCTUS ARTERIOSUS

CROSS-REFERENCE TO RELATED APPLICATION

This application claims the benefit of and priority to U.S. Provisional Application No. 62/074,647, filed on Nov. 4, 2014, the entirety of which is incorporated herein by reference.

FIELD

The present teachings relate to devices and methods of use thereof for closing a patent ductus arteriosus.

BACKGROUND

Patent ductus arteriosus (PDA) is a congenital disorder in the heart wherein a neonate's ductus arteriosus fails to close after birth. In a developing fetus, the ductus arteriosus is the vascular connection between the pulmonary artery and the aortic arch that allows most of the blood flow from the right ventricle to bypass the fetus' fluid-filled compressed lungs. During fetal development, this shunt protects the right ventricle from pumping against the high resistance in the lungs, which can lead to right ventricular failure if the ductus arteriosus closes in utero.

When the newborn takes his or her first breath, the lungs open and the pulmonary vascular resistance decreases. After birth, the lungs release bradykinin to constrict the smooth muscle wall of the ductus arteriosus and reduce blood flow through the ductus arteriosus as it narrows and completely closes, usually within the first few weeks of life. In most newborns with a patent ductus arteriosus, the blood flow is reversed from that of fetuses in utero, i.e. the blood flows from the higher-pressure aorta to the now lower-pressure pulmonary arteries.

Patent ductus arteriosus is the most common cardiac diagnosis in the neonatal period, accounting for approximately 10% of all congenital heart disease, with an incidence of at least 2-4 per 1000 pre-term births, and including up to 80% of infants with a birth weight below 2.6 lbs. If the patent ductus arteriosus does not close, long-term complications can arise, such as pulmonary hypertension, heart failure, and bacterial endocarditis. Furthermore, delayed closure of this duct is associated with increased morbidity in neonates.

An initial approach to patent ductus arteriosus closure in small premature infants for decades has been dehydration, including the use of diuretics. However, this approach compromises nutrition, the closure rates are low, and the defect often re-opens. The most common treatment today is the use of drugs known as nonselective cyclooxygenase (COX) inhibitors such as indomethacin or ibuprofen, which inhibit prostaglandin synthesis. Unfortunately, indomethacin is only approximately 60% effective at closure and can have toxic side effects, including renal failure. Ibuprofen, currently preferred, has shown no significant improvement in closure rates, however, it may have a decrease in overall risk, although the data are mixed. If drug treatments fail, surgical ligation can be performed. This, however, can involve many associated complications.

A patent ductus arteriosus can be closed by percutaneous interventional methods to avoid open heart surgery. A platinum coil can be deployed via a catheter through the femoral vein or femoral artery to induce thrombosis (coil embolization). Alternatively, a patent ductus arteriosus occluder device can be deployed from the pulmonary artery through the patent ductus arteriosus. Transcatheter occlusion of patent ductus arteriosus offers many advantages over surgery, including the fact that the procedure is better tolerated from a cardiorespiratory standpoint, is less painful, is less invasive, and has fewer complications.

The standard of care for closing a patent ductus arteriosus in this fragile patient population of small premature infants has changed very little in the past decades. Surgical closure has shown no improvement in outcomes, possibly due to the invasiveness of the procedure itself. Alternative pharmacologic options have shown no improvement in closure rates with limited decrease in adverse complications. Furthermore, percutaneous patent ductus arteriosus devices currently on the market are not ideal for patients of younger than 6 months of age or less than 6 kg of weight. These devices generally have large disc sizes, which necessitate larger delivery catheters. Thus, a safer way to close a patent ductus arteriosus in small premature babies is needed.

SUMMARY

An aspect of the present teachings provides devices for closing a patent ductus arteriosus in small premature infants. In various embodiments, the device comprises a distal annular flange portion positioned outside a first end of the ductus arteriosus, a body portion positioned inside the ductus arteriosus, and a proximal annular flange portion positioned outside a second end of the ductus arteriosus. In certain embodiments, the body portion of the device has a length which is adjustable according to the specific anatomy of a patient. For example, the body portion has a first length and a second length, and the second length is greater than the first length.

In various embodiments, the present teachings also provide a device for closing a patent ductus arteriosus where the device comprises a distal annular flange portion positioned outside a first end of the ductus arteriosus, a body portion positioned inside the ductus arteriosus, and a proximal annular flange portion positioned outside a second end of the ductus arteriosus. In some embodiments, at least one or both of the distal and proximal flange portions have the ability to pivot from a longitudinal axis of the body portion so that once positioned at the treatment location, the distal and proximal annular flanges would not impose excess pressure to the surrounding vascular tissues.

In various embodiments, the present teachings also provide a device for closing a patent ductus arteriosus where the device comprises a distal annular flange portion positioned outside a first end of the ductus arteriosus, a body portion positioned inside the ductus arteriosus, and a proximal annular flange portion positioned outside a second end of the ductus arteriosus. In some embodiments, the body portion is configured to at least partially block any blood flow through the ductus arteriosus.

DETAILED DESCRIPTION

Figure 1:
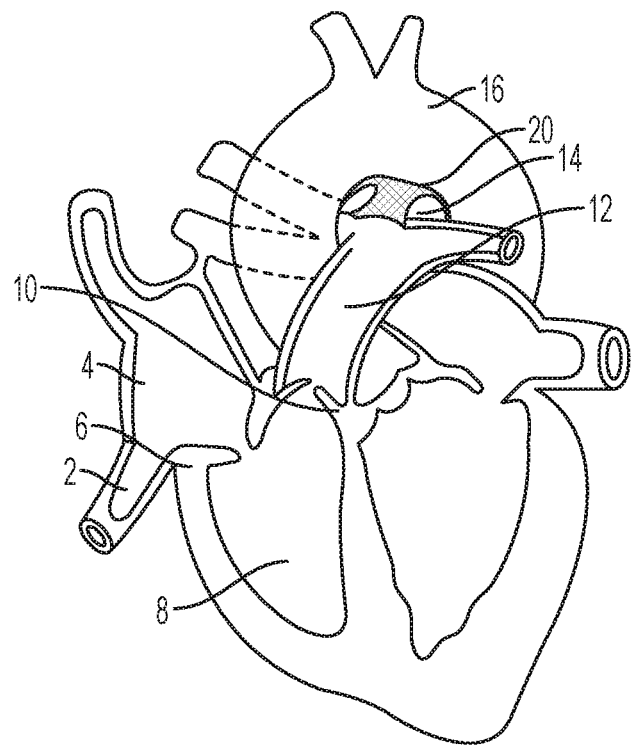
FIG. 1 is a perspective view of an exemplary ductus arteriosus closure device positioned through the ductus arteriosus between the pulmonary artery and aorta in accordance with the present teachings.

The present teachings are described more fully herein with references to the accompanying drawings, which show certain embodiments of the present teachings. The present teachings may, however, be embodied in many different forms and should not be construed as being limited to the embodiments set forth herein. Rather, these embodiments are provided to illustrate various aspects of the present teachings. Unless specifically noted otherwise, like numbers refer to like elements throughout.

The present teachings provide a device and methods of using this device to percutaneously close a patent arterial duct. According to some embodiments of the present teachings, the device includes portions, at least one of which has a relatively flat profile. The portion of a relatively flat profile can be located in the descending aorta and/or the pulmonary artery. In some embodiments, the device can be delivered through a small catheter. In some embodiments, the device is echogenic.

As used herein, when terms "distal" and "proximal" are used to refer to a portion of a device, they mostly refer to the device in its elongated delivery configuration. The term "proximal" shall mean close to the operator (less into the body) and "distal" shall mean remote from the operator (further into the body). In positioning a medical device from a downstream access point, "distal" is more upstream and "proximal" is more downstream.

As explained in further detail below, various embodiments of the present teachings provide medical devices for closing a patent ductus arteriosus. In some embodiments, a medical device of the present teachings includes a body portion and a flange. In certain embodiments, the device comprises a body portion and two flanges and the body portion is coupled to and located between the two flanges. In particular embodiments, at least one flange is a retention flange. In particular embodiments, both the flanges are retention flanges. For ease of reference, these flanges include a distal flange and a proximal flange.

In various embodiments, the device of the present teachings includes a distal portion and a proximal portion. As discussed in further detail herein, the device can have a delivery configuration and a deployment configuration. In some embodiments, at least one or both of the distal and proximal portions in their deployment configuration has a generally flange-like profile. This generally flange-like profile, for example, would not impede blood flow when the distal portion and/or the proximal portion rest against the vascular wall inside the pulmonary artery or the aorta. In some embodiments, upon proper deployment at the treatment location, the body portion of the device is positioned through the ductus arteriosus; the distal portion is positioned against the vascular wall on one side of the ductus arteriosus; and the proximal portion is positioned against the vascular wall on the other side of the ductus arteriosus.

According to some embodiments, the device is delivered from the pulmonary artery across the ductus arteriosus. In some embodiments, the device is deployed so that the distal flange is positioned against the aorta vascular wall and the proximal flange is positioned against the pulmonary artery vascular wall. In other embodiments, the device is delivered from the aorta across the ductus arteriosus. In some embodiments, the device is then deployed so that the distal flange is positioned against the pulmonary artery vascular wall and the proximal flange is positioned against the aorta vascular wall.

According to some embodiments, in its deployment configuration, the device is secured at a treatment location by at least one of the distal and proximal flanges, for example, by applying compression force against the vascular wall. This can be achieved by the flange inside the aorta being positioned against the vascular wall. According to another embodiment, the device is secured at the treatment location by the body portion being fixed against the tissues inside the ductus arteriosus.

In various embodiments, a medical device of the present teachings has an elongated profile and a preset profile. In some embodiments, the medical device is extended into the elongated profile for percutaneous delivery (sometimes referred to as a delivery profile) and resumes the preset profile after deployment (sometimes referred to as a deployment profile). In some embodiments, the device is configured to transition from a delivery profile to a deployment profile through self-expansion or mechanical actuations. In some embodiments, during deployment, both the distal and proximal retention portions of the device expand radially while the device contracts longitudinally. In certain embodiments, one or both the distal and proximal retention portions of the device contract longitudinally. FIG. 1 illustrates an embodiment of the present teachings being positioned through the ductus arteriosus (14). In this embodiment, the device (20) has a first retention flange configured to be positioned against the vascular wall in the aorta (16) around the ductus arteriosus (14), a second retention flange configured to be positioned against the vascular wall in the pulmonary artery (12) around the ductus arteriosus (14), and a body portion between the two flanges configured to at least partially block the ductus arteriosus (14) and/or restrict the blood flow in the ductus arteriosus (14). The deployed device (20) according to some embodiments of the present teachings has an expanded first flange, an expanded second flange, and a body portion between the two flanges.

Figure 2:
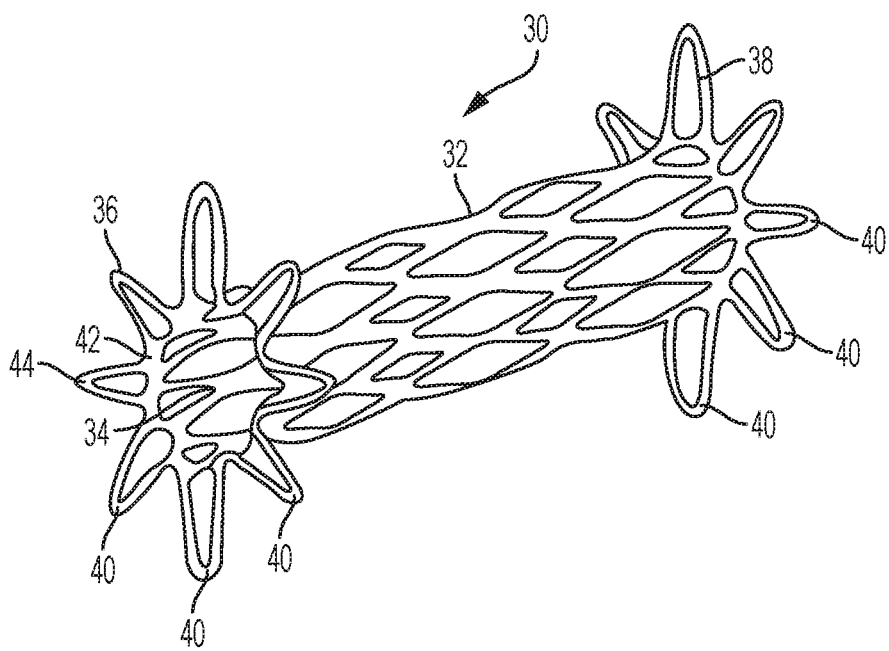
FIG. 2 is a perspective view of an exemplary ductus arteriosus closure device in accordance with the present teachings.

FIGS. 2-7 illustrate various embodiments of the body portion of a patent ductus arteriosus closure device according to the present teachings. FIG. 2 illustrates an embodiment of the present teachings where the body portion (32) has a generally cylindrical shape. In FIG. 2, the body portion (32) has a central lumen (34) extending throughout the body portion (32). In some embodiments, the central lumen (34)

of the body portion (32) is configured to allow a limited amount of blood flow in the event that the patient's condition requires it.

Figure 3A:
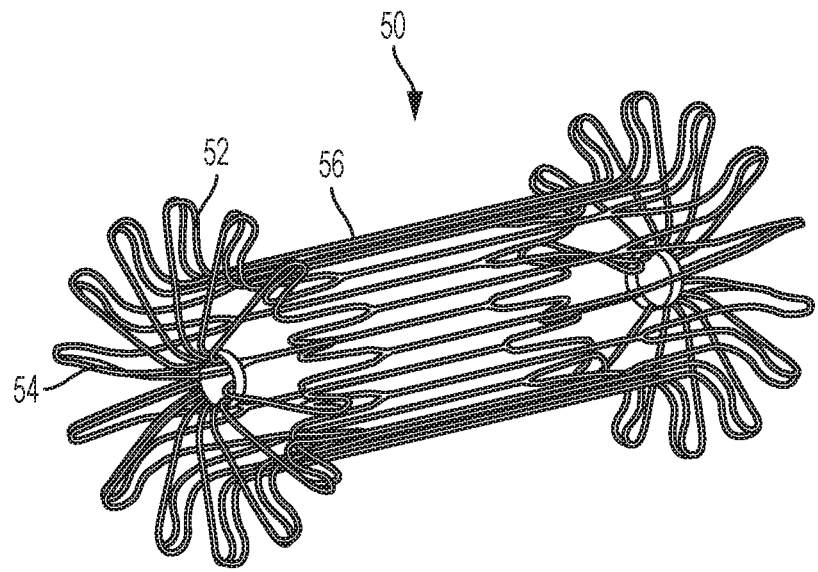
FIGS. 3a and 3b are perspective views of two exemplary ductus arteriosus closure devices in accordance with the present teachings.
Figure 3B:
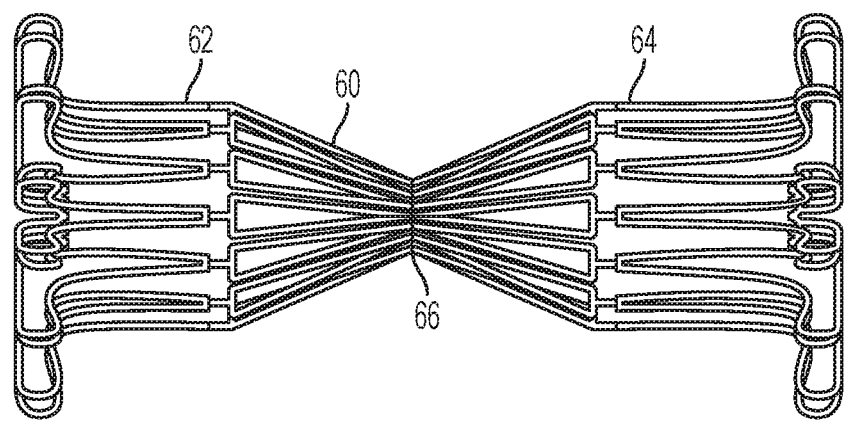

According to some embodiments of the present teachings, the body portion of the device is configured to impede the blood flow through the ductus arteriosus (14). FIG. 3b illustrates an embodiment that has a generally funnel shaped distal section of a body portion (62), a generally funnel shaped proximal section (64), and a waist section (66) between the proximal and distal sections (62, 64). In this embodiment, the narrowed waist (66) section of the body portion (60) is configured to limit the blood flow, or alternatively, completely block the blood flow from the aorta (16) to the pulmonary artery (12). In some embodiments, as shown in FIG. 3b, the cross section of the body portion (60) varies from section to section. In certain embodiments, the cross section at the distal section (62) and proximal section (64) of the body portion (60) is greater than the cross section of the waist section (66). One skilled in the art would understand that although FIG. 3b illustrates generally funnel shaped distal and proximal sections (62, 64), other shapes/profiles can also be incorporated. For example, the distal and proximal sections of the body portion of the device can be configured in the general shape of a cone. Thus, the specific embodiments disclosed here should not be viewed as limiting to the scope of the present teachings.

Figure 4:
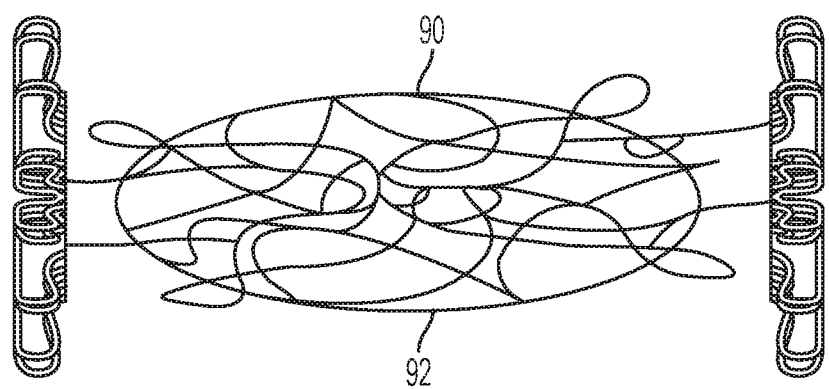
FIG. 4 is a perspective view of an exemplary ductus arteriosus closure device in accordance with the present teachings.

Other mechanism can also be incorporated to at least partially block the flood flow through the ductus arteriosus (14). FIG. 4 illustrates an embodiment of such body portion (90). In this illustrated embodiment, the body portion (90) is constructed of a single strand which curls into a wire bundle (92) upon deployment inside the ductus arteriosus (14), thereby blocking the blood flow. The term "strand" used herein can be wires, cords, fibers, yarns, filaments, cables, threads, coil, spring, or the like, and these terms may be used interchangeably. According to one embodiment, the strand used to form the device has a general diameter from about 0.02 mm to about 1 mm. The strand that makes up the body portion is pre-formed as a wire bundle. According to some embodiments, the body portion (90) extends longitudinally to fit inside a delivery catheter. In certain embodiments, once the body portion (90) is exposed, or pushed, outside of the delivery catheter, the strand resumes its pre-formed relaxed bundled profile inside the ductus arteriosus (14) and at least blocks the blood flow in the ductus arteriosus (14).

Figure 5:
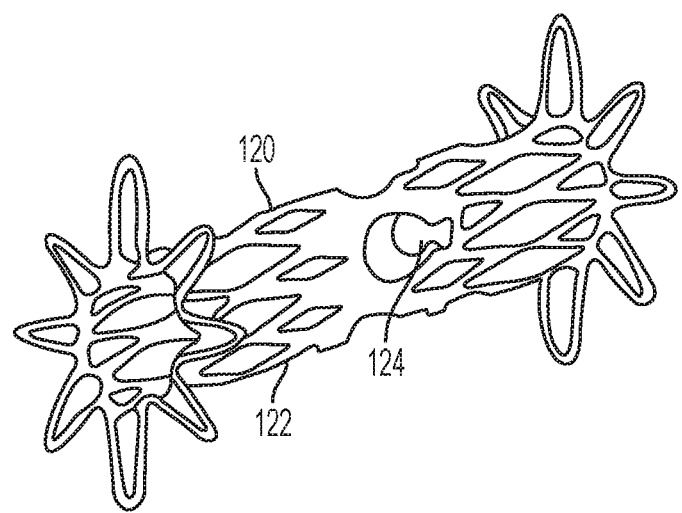
FIG. 5 is a perspective view of an exemplary ductus arteriosus closure device in accordance with the present teachings.

Although FIGS. 3b and 4 illustrate two embodiments of the body portion of the present teachings, one skilled in the art would understand that other mechanisms can also be employed to achieve the purpose of blocking the blood flow. For example, the body portion can be made of a solid piece. In another embodiment, as shown in FIG. 5, the body portion (120) has a tubular (122) body with multiple tabs (124) each made by a "C" or "U" slit and when the device is in its deployment configuration, the tabs (124) bend radially inward to block the tubular lumen and obstruct the blood flow. One skilled in the art would understand the specific embodiments discussed herein should not be viewed as limiting.

In certain circumstances, it is beneficial for a patient if the blood flow through a ductus arteriosus (14) is gradually limited, instead of being blocked. For such a patient, a clinician can deploy a device with a tubular body portion, such as the example shown in FIG. 2, inside the ductus arteriosus (14) to allow some residual flow, and later deploy a plug of the same or a different material inside the tubular body portion to block the blood flow.

Referring back to FIGS. 2 and 3b, according to some embodiments of the present teachings, the body portion can be constructed of a solid tube, and in other embodiments, the body portion can include an open mesh construct along its cylindrical body. According to some embodiments of the present teachings, the mesh incorporates openings with diamond, oval, "V", "C", "L", "U", or any other shapes to allow the body portion to extend longitudinally during delivery and expand radially upon deployment. In some embodiments, the cylindrical body portion is configured to have the same size and shape at its delivery configuration and its deployed configurations. In other embodiments, the open mesh constructs allow the body portion of the device to extend longitudinally into a longer profile with a smaller cross section than its deployed profile.

Figure 6:
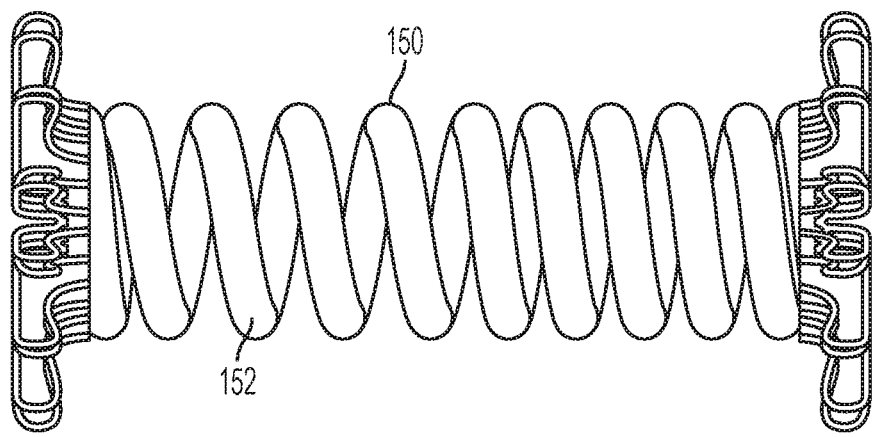
FIG. 6 is a perspective view of an exemplary ductus arteriosus closure device in accordance with the present teachings.

FIG. 6 illustrates another embodiment of the body portion (150) of a device of the present teachings where the body portion (150) is configured to include a length adjustable mechanism so that the body portion (150) of the device can alter its length. For example, the length of the body portion (150) at its deployment configuration can be greater than that at its natural relaxed configuration. For example, as illustrated in FIG. 6, the body portion (150) of the device has a general shape of a coil (152), which has a general relaxed length and a general relaxed cross sectional profile, and an extended length and a smaller cross sectional profile. One skilled in the art would understand that cuts, shapes, or patterns which achieve the same length adjustment purpose can be incorporated to the body portion. For example, the body portion can have a zigzag, helical, or spiral cutting pattern, or other slitting form in order to make the body portion stretchable.

Figure 7:
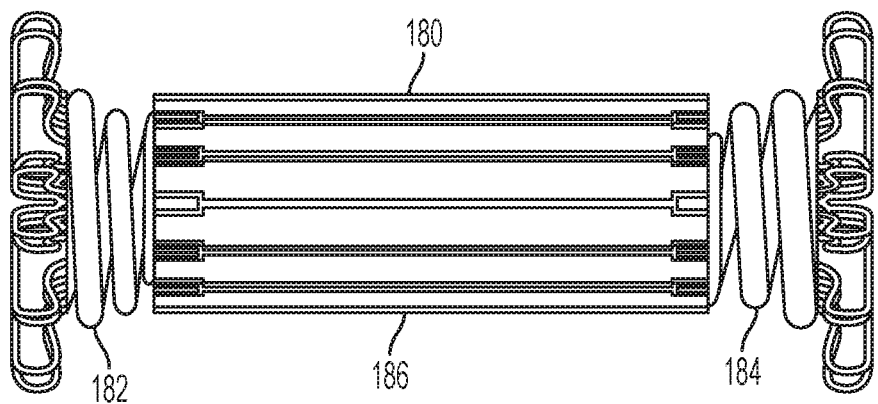
FIG. 7 is a perspective view of an exemplary ductus arteriosus closure device in accordance with the present teachings.
Figure 8:
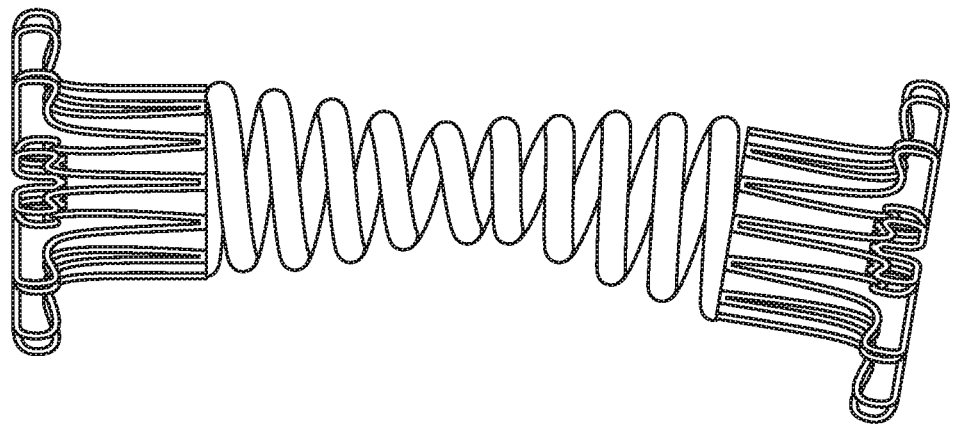
FIG. 8 is a perspective view of an exemplary ductus arteriosus closure device in accordance with the present teachings.

According to various embodiments of the present teachings, some of which are shown in FIGS. 2-8, the body portion of the device has multiple sections. In some embodiments, the body portion of the device includes a proximal section and a distal portion. In some embodiments, the body portion of the device includes a middle section between the proximal and distal sections. In certain embodiments, the proximal section of the body portion is connected with the proximal flange portion of the device according to the present teachings. In certain embodiments, the distal section of the body portion is connected with a distal flange portion of the device according to the present teachings. In certain embodiments, the multiple sections of the body portion are constructed of different materials. In certain embodiments, the multiple sections of the body portion have different configurations. For example, as shown in FIGS. 7 and 8, the middle section is different from both the distal and proximal sections. As the skilled artisan would understand and appreciate, the differences in the multiple sections of the body portion can serve different purposes, some of which are discussed herein.

According to some embodiments of the present teachings, the body portion of the device has multiple sections each having a different profile and configured for a different function. FIG. 3b illustrates one embodiment of such body portion (60) where a center waist portion (66) is configured to impede blood flow while the distal and proximal sections (62, 64) are configured to secure the device inside the ductus arteriosus (14). FIG. 7 illustrates another embodiment where the distal and proximal spiral/coil sections (182, 184) of the body portion (180) are configured to be stretchable, and thereby achieving the length adjustment purpose, and a center tubular portion (186) is configured to secure the device inside the ductus arteriosus (14).

One skilled in the art would understand that FIGS. 2-7 merely illustrate various embodiments of the present teachings. And these embodiments, as well as other embodiments that are known to those skilled in the field or are obvious variants or equivalents of the disclosed embodiments, can be incorporated and combined without traversing the scope of the present teachings. For example, various embodiments can be combined so that the length of the body portion can be adjusted. What have been disclosed herein should not be viewed as limiting.

According to some embodiments of the present teachings, the body portion of the device has a relaxed length of 2-15 mm. According to some embodiments of the present teachings, the body portion is configured to be able to stretch from 105% to 1000% of its relaxed length. According to another embodiment, the body portion is configured to be able to stretch by a relatively small force. For example, when the device is deployed at a treatment location, with the distal and proximal flanges positioned against vascular wall at each end of the ductus arteriosus (14), the body portion is stretched to accommodate the length of the ductus arteriosus (14) without applying excess pressure on the vascular walls.

In some embodiments, the body portion is configured to fit inside the ductus arteriosus (14). In another embodiment, the body portion is configured to apply radial pressure to the surrounding tissues from inside the ductus arteriosus (14). In another embodiment, the body portion also includes some tissue anchoring features along its exterior surface. Examples of the tissue anchoring features include spikes, barbs, or other tissue anchors, known to those skilled in the field to secure the body portion of a device inside the ductus arteriosus (14). Alternatively, the exterior surface of the body portion can incorporate a texture or surface roughness for better positioning inside the ductus arteriosus (14) and better attachment to cells.

According to some embodiments of the present teachings, the deployed body portion of the device has a relaxed cross section profile with a general diameter of 1-6 mm. In some embodiments, the body portion of the device extends longitudinally so that the cross section of the body portion can reduce its dimension by up to 85% in order to fit inside a delivery catheter, for example a 3 French catheter.

In various embodiments, a device of the present teachings includes a distal flange, a proximal flange, and a body portion as discussed herein. In some embodiments, at least one of the distal flange, the proximal flange, and the body portion has an open mesh-like structure. In particular embodiments, the entire device has an open mesh-like structure. In such embodiments, the mesh can be formed from a hollow tube that has been slotted, for example, by using a machining laser, a water drill, or other methods, and then expanded to form the open structure. Alternatively, the device may also be formed of a woven, knitted, or braided tubular metallic fabric made out of metallic strands. In other embodiments of the present teachings, the mesh can be formed from wires that are pre-bent into the desired shape and then bonded together to by welding or adhesive bonding. They can also be welded using a resistance welding technique or an arc welding technique, preferably while in an inert environment and with cooling to control the grain structure in and around the weld sites. These joints can be conditioned after the welding procedure to reduce the grain sizes by using coining or upset forging to optimize the fatigue performance. For example, the body portion can be formed by two or more pre-bent wires (e.g., parallel wires as shown in FIG. 3a, or having a generally funnel shaped distal section, a generally funnel shaped proximal section (64), and a waist section as shown in FIG. 3b) that are bonded together. In some embodiments, the body portion includes at least two parallel pre-bent wires bonded together.

Without being limited to any particular theory, the ductus arteriosus can vary in sizes and dimensions in patients. Accordingly, it can be desirable to have a ductus arteriosus closure device to fit into the ductus arteriosus of varying sizes and dimensions. An aspect of the present teachings relate to a device having a distal flange portion and a body portion where the body portion is adjustable independent of the distal flange portion. As shown in FIGS. 2-8, in various embodiments, the body portion is adjustable independent of the distal flange portion or the proximal flange portion of a device of the present teachings. In some embodiments, the body portion is adjustable independent of the distal flange portion a device of the present teachings. In some embodiments, the body portion is adjustable independent of the proximal flange portion a device of the present teachings. In some embodiments, the body portion is adjustable lengthwise (i.e., in directions that are substantially along the longitudinal axis of the body portion). In some embodiments, the body portion is adjustable crosswise (i.e., in directions that are substantially perpendicular to the longitudinal axis of the body portion). In some embodiments, the body portion adjusts to the anatomy of the ductus arteriosus independent of the distal flange portion. In some embodiments, the body portion adjusts to the anatomy of the ductus arteriosus independent of the proximal flange portion.

Continuing referring to FIG. 2, according to some embodiments of the present teachings, the device (30) has a distal annular flange (36) and a proximal annular flange (38). As shown in FIG. 2, the exemplary distal and proximal annular flanges (36, 38) each includes multiple flange segments (40) with fixed ends (42) and free ends (44). The fixed ends (42) connect to adjacent ends of the body portion (32) as shown, and the free ends (44) extends radially outward from the longitudinal axis of the body portion (32) when the device (30) is deployed, for example, at a treatment location. In some embodiments, at least some of the distal annular flanges extend substantially in direction substantially perpendicular to the longitudinal axis of the distal section of the body portion. In some embodiments, at least some of the proximal annular flanges extend substantially in direction substantially perpendicular to the longitudinal axis of the proximal section of the body portion. In According to some embodiments of the present teachings, as shown in FIG. 2, the flange segments (40) are formed of two individual strut elements. One skilled in the art would recognize that the flange segments also can be formed of a single element, or more than two struts. Thus the specific embodiment shown here should not be viewed as limiting.

FIG. 3a illustrates another embodiment of the device (50) where the proximal annular flange (52) also connects to a proximal retrieval portion (54). According to some embodiments of the present teachings, the proximal retrieval portion (54) is configured to form an attachment between the device (50) and the delivery catheter so that a clinician can have full control of the device during delivery, deployment, or retrieval, if necessary. As shown in FIG. 3a, according to some embodiments, the proximal retrieval portion (54) also includes multiple retrieval struts with fixed ends connecting to the free ends of the proximal flange segments. As the device is fully deployed, the fixed ends of the proximal retrieval struts are drawn radially outward by the free ends of the proximal flange segments, while the free ends of the proximal retrieval struts remain more radially inward than the fixed ends of the proximal retrieval struts, and closer to the radial center of the body portion. Although the proximal retrieval portion (54) in this exemplary embodiment is made of multiple single retrieval struts, one skilled in the art would understand that such configuration, such as multiple retrieval flanges made up by at least two struts, can also be incorporated in the design. Thus the scope of the present teaching should not be limited to the embodiments discussed herein.

According to some embodiments of the present teachings, the free ends of the proximal retrieval struts are configured to function as an attachment mechanism between the device and its delivery catheter. For example, as shown in FIG. 3a, the free ends of the proximal retrieval struts can be gathered together at a place close to the radial center of the body portion (56), forming a thread connector to be attached to a matching thread connector at a distal end of a delivery catheter. One advantage of such embodiments is that the deployed proximal retrieval portion (54) of the device (50) also serves to impede the blood flow through the ductus arteriosus (14). The degree of blood flow blockage depends upon the amount of proximal retrieval struts incorporated. Many known attachment mechanisms can be incorporated with this embodiment. Thus the specific embodiments disclosed herein should not be viewed as limiting. In other embodiments, the free ends of the proximal retrieval struts can end at a place radially outward from the center lumen of the body portion of the device. In such embodiments, other attachment mechanisms between the device and the delivery catheter can be incorporated According to some embodiments of the present teachings, in the deployed configuration, the proximal retrieval portion maintains a small profile at its longitudinal direction when the proximal retrieval portion fully expands radially. In these particular embodiments, when the device is deployed at the treatment location, the proximal retrieval portion and the proximal flange together form a relatively small profile outside of the ductus arteriosus (14) and inside the vasculature.

In some embodiments, the proximal retrieval portion is configured to allow a clinician to maintain control of the device. In certain embodiments, while the distal and/or proximal flange portions are fully deployed in vivo, the device does not experience any excess stress caused by its connection to a delivery catheter. In another embodiment, the proximal retrieval portion is configured to be close to or around the center of the body portion without deforming the proximal flange portion.

In another embodiment, the proximal retrieval portion is configured to allow the device to be retrieved into a retrieval catheter smoothly. In yet another embodiment, the proximal retrieval portion is configured to allow the device to be retrieved into a retrieval catheter without any part of the device caught by the distal end of the catheter. In another embodiment, the proximal retrieval portion is configured to minimize the retrieval force required for retrieving the deployed device into a catheter. According to some embodiments, the length of the proximal retrieval struts can vary depending on the overall size of the device and the ability to achieve the above-mentioned functions.

According to some embodiments, the proximal retrieval portion is configured to be attached by a flexible delivery mechanism. In one embodiment, a delivery filament, such as a wire or a suture, extends through one or more retrieval attachment mechanisms with both ends of the filament being controlled by a clinician. Upon deployment, one end of the delivery filament is loosened and the other end of the delivery filament is retracted proximally so that the entire flexible delivery filament is removed from the body. One skilled in the art would understand that a flexible delivery filament allows the device to fully deploy at a treatment location, while still under the control of the clinician, so that the deployment can be assessed and the device can be retrieved if necessary.

According to some embodiments, the proximal retrieval portion is configured to be attached by a relatively rigid delivery mechanism. In one embodiment, the relatively rigid delivery mechanism is a delivery shaft with threaded attachment or notches at its distal end for hosting or connecting the proximal retrieval portion of a device of the present teachings. During delivery, the proximal retrieval portion is secured to the distal end of the delivery shaft; and upon deployment, the proximal retrieval portion is released from the delivery shaft. One skilled in the art would understand that a relatively rigid delivery shaft can push the device distally inside the delivery catheter to deploy the device.

One skilled in the art would understand that other configurations of proximal retrieval portion can also be incorporated to allow a ductus arteriosus (14) device to be retrieved and repositioned. Additionally, one skilled in the art would understand that other configurations of proximal retrieval portion can also be incorporated to allow a clinician to assess the final position of the device while maintaining control of the device.

One skilled in the art would understand that exemplary embodiments illustrated in FIGS. 2 and 3a are not intended to limit the scope of the present teachings. Devices can have only one flange, preferably positioned against the vascular wall inside the aorta, which can be a relatively flat annular flange with or without a retrieval portion. Alternatively, devices with combined flange configuration are also within the spirit of present teachings. For example, a device can have both distal and a proximal retrieval portion. In some embodiments, a device of the present teachings does not have any retrieval portion.

According to some embodiments of the present teachings, in the event where a device has both a proximal annular flange and a distal annular flange, the distal and proximal annular flanges have the same number of flange segments. Alternatively, the distal and proximal annular flanges have different numbers of flange segments.

According to some embodiments of the present teachings, in the event where a device has both a proximal annular flange and a distal annular flange, the distal flange segments are configured to be radially offset from the proximal flange segments. Alternatively, in the event where a device has both proximal and distal annular flanges, the distal flange segments are configured to be radially aligned with the proximal flange segments.

Examples of the annular flange and flange segments described in conjunction with the drawings of the present teachings have some similarities to those in U.S. Pat. No. 8,043,360, filed on Mar. 8, 2010, entitled Devices, Systems and Methods to Treat Heart Failure, United States Patent Application Publication No. 20140012368, filed on May 15, 2013, entitled Devices and methods for retrievable intra-atrial implants, U.S. Patent Application Ser. No. 62/004,160, filed on May 28, 2014, entitled Devices and Methods for Treating Heart Failure, each of which is incorporated by reference herein in its entirety.

The flange segments may generally be rectangular in cross section, circular in cross section, oval in cross section, or some other geometric shape in cross section. According to some embodiments of the present teachings, the flanges and/or the segments are integral with the body portion. That is, they need not be necessarily "attached" thereto but may be fabricated from the same material that is used to construct the body portion (including in the manners described herein) and thus may be contiguous therewith.

According to some embodiments of the present teachings, the flange segments are designed to be more flexible than the body portion. The increased flexibility may be achieved in several ways. In some embodiments, the overall cross sectional size of the strut elements that make up the flange segments is smaller relative to the corresponding dimension of the struts (or strands) that make up the body portion. Alternatively, one or a few specific dimensions of the struts elements that make up the flange segments is altered to achieve a desired flexibility, for example, the width of the struts for the flange segments are reduced compared to that of the body portion. In other embodiments, the struts for the flange elements can be made from a different material, having a greater flexibility, than that of the body portion. The choice of materials based on their flexibility will be apparent to those skilled in the art. In the ways described above, the flange segments can achieve greater flexibility than the body portion (or the remaining portion of the flange segment or the flange itself as the case may be) thereby reducing the probability of damage to the tissue of the vascular wall where the flanges are positioned against while allowing the body portion to maintain a strong outward force against the interior of the ductus arteriosus (14) and thus decrease the probability of the device becoming dislodged.

In some embodiments, the deployed distal flange portion has the same size as the deployed proximal flange portion. In other embodiments, the expanded distal flange portion of the device is slightly larger radially than the expanded proximal flange portion or vice versa. In certain embodiments, the size difference is to account for the typical pressure gradient from one side of the ductus arteriosus (14) to the other, and to facilitate deployment. In some embodiments, the distal flange portion has a general diameter of 3-12 mm upon deployment. In another embodiment, the deployed proximal flange portion has a general diameter of 3-12 mm upon deployment. According to some embodiments, upon deployment, the diameter of the deployed body portion of the device is about 50-70% of the overall diameter of the deployed distal flange portion. According to another embodiment, in the event where the patent ductus arteriosus closure device has only one flange, upon deployment, the diameter of the deployed body portion of the device is about 50-70% of the overall diameter of the deployed flange portion.

According to some embodiments, when deployed in vivo, the radially expanded portions distal and proximal to the body portion of the device are configured to apply compression force against both sides of the ductus arteriosus (14). In certain embodiments, the device is secured across the ductus arteriosus (14), for example, by the compression force against the vascular wall outside of at least one or both sides of the ductus arteriosus (14). In some embodiments, the compression is applied by the radially expanded distal and proximal flange portions. In another embodiment, the compression is applied by a radially outward portion of the distal flange portion and/or the proximal flange portions. According to some embodiments, upon deployment, the body portion also applies a compression force along its outside tubular surface toward the surrounding vascular tissues inside the ductus arteriosus (14). In another embodiment, the body portion is in contact with the surrounding tissues without applying a significant stress toward the surround heart tissues.

According to some embodiments of the present teachings, one or both distal and proximal flanges of the device are configured to pivot from the body portion. Since the body anatomy differs from one patient to another, once a device of the present teachings is deployed at a treatment location, the distal and proximal flanges parallel to each other may apply excess pressure to the surrounding tissue due to the nature of the anatomy. Thus, to avoid excess compression against the vascular wall and to allow the discs to sit flat on the tissue to promote a complete closure while avoiding obstructing the aorta or pulmonary artery (12) or inducing thrombosis, according to some embodiments, at least one of the distal and proximal flanges is configured to pivot against the body portion of the device. FIG. 8 illustrates one embodiment where both the distal and proximal flanges are configured to be able to pivot from the body portion of the device at an angle "θ." Although FIG. 8 illustrates that both the distal and proximal flanges pivot from the body portion of the device, one skilled in the art would recognize that such pivoting, in large part, is dictated by the anatomy of the treatment site. That is, once the device is deployed at treatment site, either the proximal flange or the distal flange, or both the flanges would turn relative to the longitudinal axis of the body portion of the device, i.e. pivot, in order to rest against the vascular wall without applying pressure on the tissue surface. Allowing the flanges to pivot is also important to promote complete closure by having them seal flat against the tissue on both sides of the ductus while avoiding any obstruction of the lumen of the descending aorta or pulmonary artery (12), which could compromise flow and/or result in thrombus formation.

According to some embodiments of the present teachings, the pivotability of the distal and/or proximal flanges are achieved by a flexible section of the body portion such as shown in FIG. 8. FIG. 8 illustrates that the body portion of the device. The body portion includes a section of flexible coil which allows the portions of the device (including the section of the body portion and the annular flange connecting to such section) on both sides of the coil to deflect away from the longitudinal axis of the body portion as directed by the anatomy. One skilled in the art would also recognize that such coil section of the body portion of the device also serves as length adjustment of the overall deployed body portion and ultimately the device. Other mechanisms could also be incorporated to achieve the pivotability purpose. For example, as shown in FIG. 7, the body portion of the device can incorporate coil sections on both ends and the coil sections can further attach to the respective annular flanges.

Although FIGS. 7-8 illustrate embodiments where pivotability is achieved by incorporating coil sections to the body portion, other means, including section(s) with cutting patterns, can also be used to achieve the same purpose. One skilled in the art would understand that other designs, such as the one shown in FIG. 4, also produce a patent ductus arteriosus closure device with inherent pivotability on its flanges. Other means to achieve pivotability should also be considered as within the scope of the present teachings, for example, the inherent characteristics of the material, post-fabrication treatment to the device, or other mechanical design.

According to some embodiments, a device of the present teachings is manufactured by laser cutting a biocompatible metal tube. According to some embodiments, the device is made of a biocompatible metal or polymer. In various embodiments, the entire device is made of a biocompatible metal or polymer. In some embodiments, the device in its entirety or portion(s) thereof, for example, those with curved/bent deployment configurations, is made of an elastic material, a super-elastic material, or a shape-memory alloy. As a result, for example, the above portions can be distorted into a generally straightened profile during the delivery process and resume and maintain its intended profile in vivo once the device is deployed from a delivery catheter. In some embodiments, the device is made of stainless steel, nitinol, Titanium, Elgiloy, Vitalium, Mobilium, Ticonium, Platinore, Stellite, Tantalum, Platinum, Hastelloy, CoCr, CoCrNi alloys (e.g., trade name Phynox), MP35N, or CoCrMo alloys, any other metallic alloys, or a mixture thereof. Alternatively, in some embodiments, a part of the device or the entire device is made of a polymer, such as PTFE, UHMPE, HDPE, polypropylene, polysulfone, or other biocompatible plastic. The surface finish of the device can be textured to induce tissue response and tissue in-growth for improved stabilization. Alternatively, a part of or the entirety of the device can be fabricated from a resorbable polymer. In some embodiments, the resorbable polymer includes polyactic acid, polyglycolic acid, polycaprolactone, a combination of two or more of the above or a variety of other resorbable polymers that are well known to those skilled in the art.

According to one embodiment of the present teachings, the device is fabricated from a tubular form and then shaped to its final configuration. In one embodiment, if a sufficiently elastic and resilient material, such as nitinol, is used, the structure is preformed into the finished shape and elastically deformed. In some embodiments, the device is stowed in a delivery device during the delivery and the device elastically recovers its pre-formed shape upon deployment. In some embodiments, one, some, or all portions of the device are manually expanded to the desired diameter and/or curved to a pre-set shape. In certain embodiments, one, some, or all portions of the device are heat set in an oven while constrained to the desired shape.

According to one embodiment of the present teachings, at least one portion of the device expands radially upon or after being deployed in vivo. According to one embodiment of the present teachings, after the device is deployed, the radial expansion of at least one portion of the device is due to the elastic nature of the material. According to another embodiment of the present teachings, the radial expansion of at least one portion of the device is due to its pre-set thermal shape memory of the material. According to yet another embodiment of the present teachings, during the deployment of the device, at least one portion of the device is manually expanded radially via a balloon.

In the embodiments where the device is expanded in vivo via a balloon, the device can be mounted over a balloon catheter, where the inflatable balloon is positioned inside the body portion of the device. In these particular embodiments, after the device is deployed at a treatment location, the balloon is then inflated and expands the body portion of the device; and upon reaching a desired size, the balloon is then deflated and retracted out of the device and into the delivery catheter.

According to various embodiments of the present teachings, one or more radio-opaque markers are used. Without attempting to limit to any particular function, these radio-opaque markers can be visualized by using radiographic imaging equipment such as X-ray or fluoroscopy, magnetic resonance, ultrasound, or other imaging techniques known to one of ordinarily skilled in the art. One or more markers as disclosed herein can be applied to any part of a device or a delivery system of the present teachings. A radio-opaque marker can be welded, sewed, adhered, swaged, riveted, coated, otherwise placed, and secured in or on the device. The radio-opaque marker may be made of tantalum, tungsten, platinum, irridium, gold, or alloys of these materials or other materials that are known to those skilled in the art. The radio-opaque marker can also be made of numerous paramagnetic materials, including one or more elements with atomic numbers 21-29, 42, 44, and 58-70, such as chromium (III), manganese (II), iron (III), iron (II), cobalt (II), copper (II), nickel (II), praesodymium (III), neodymium (III), samarium (III), ytterbium (III), gadolinium (III), terbium (III), dysprosium (III), holmium (III) and erbium (III), or other MR visible materials that are known to those skilled in the arts.

One skilled in the art will recognize that the device described herein may be used with a tissue scaffold, various drugs, growth factors, and/or other agents to control the tissue in-growth at the ductus arteriosus (14) so that restricting and/or blocking the blood flow through the ductus arteriosus (14) can be controlled. The tissue scaffold can be made of any flexible, biocompatible material capable of controlling host tissue growth including, but not limited to, polyester fabrics, Teflon-based materials, such as ePTFE, polyurethanes, metallic materials, polyvinyl alcohol (PVA), extracellular matrix (ECM) isolated from a mammalian tissue, or other bioengineered materials, bioabsorbable polymers, or other natural materials (e.g., collagen), or combinations of these materials. Furthermore, the surface of the tissue scaffold can be modified with biological, pharmaceutical and/or other active ingredients, such as anti-coagulants, anti-thrombogenic agents, cells, growth factors and/or drugs to diminish calcifications, protein deposition, and thrombus; control and direct tissue growth by stimulating an irritation response to induce cell proliferation in one area and discourage cell proliferation in the other area. The tissue scaffold can be attached to the entire device or the body portion of the device along by sutures, heat treatment, adhesives, or any other bonding process.

Drugs, growth factors, and/or other agents to control the tissue in-growth at the ductus arteriosus (14) is selected from Adenovirus with or without genetic material, Angiogenic agents, Angiotensin Converting Enzyme Inhibitors (ACE inhibitors), Angiotensin II antagonists, Anti-angiogenic agents, Antiarrhythmics, Anti-bacterial agents, Antibiotics (including, for example, Erythromycin, Penicillin), Anti-coagulants (including, for example, Heparin), Anti-growth factors, Anti-inflammatory agents (including, for example, Dexamethasone, Aspirin, Hydrocortisone), Antioxidants, Anti-platelet agents, Forskolin. Anti-proliferation agents, Anti-rejection agents, Rapamycin, Anti-restenosis agents, Antisense, Anti-thrombogenic agents, Argatroban Hirudin, GP IIb/IIIa inhibitors, Antivirus drugs, Arteriogenesis agents, acidic fibroblast growth factor (aFGF), angiogenin, angiotropin, basic fibroblast growth factor (bFGF), Bone morphogenic proteins (BMP), epidermal growth factor (EGF), fibrin, granulocyte-macrophage colony stimulating factor (GM-CSF), hepatocyte growth factor (HGF), HIF-1, insulin growth factor-1 (IGF-1), interleukin-8 (IL-8), MAC-I; nicotinamide platelet-derived endothelial cell growth factor (PD-ECGF), platelet-derived growth factor (PDGF), transforming growth factors alpha & beta (TGF-a, TGF-b), tumor necrosis factor alpha (TNF-a), vascular endothelial growth factor (VEGF), vascular permeability factor (VPF), Bacteria Beta blocker, Blood clotting factor. Calcium channel blockers, Carcinogens, Cells, Bone marrow cells, Blood cells, Stem Cells, Umbilical cord cells, Fat cells, Chemotherapeutic agents (e.g., Ceramide, Taxol, Cisplatin), Cholesterol reducers, Chondroitin Collagen Inhibitors, Colony stimulating factor, Coumadin, Cytokines, prostaglandins, Dentin Etretinate Genetic material, Glucosamine, Glycosaminoglycans; L-703, 081, Growth factor antagonists or inhibitors, Growth factors, Autologous Growth Factors; Basic fibroblast growth factor (bFGF), Bovine Derived Growth Factors, Cartilage Derived Growth Factors (CDF), Endothelial Cell Growth Factor (ECGF), Fibroblast Growth Factors (FGF), Nerve growth factor (NGF), Recombinant NGF (rhNGF), Recombinant Growth Factors, Tissue Derived Cytokines, Tissue necrosis factor (TNF), Growth hormones, Heparin sulfate protcoglycan, HMC-CoA reductase inhibitors (statins), Hormones, Erythropoietin, Immoxidal, Immunosuppressant agents, inflammatory mediator, Insulin, Interleukins, Lipid lowering agents, Lipoproteins, Low-molecular weight heparin, Lymphocytes, Lysine, Morphogens Nitric oxide (NO), Nucleotides, Peptides, PR39, Proteins, Prostaglandins, Proteoglycans, Perlecan Radioactive materials, Iodine-125, Iodine-131, Iridium-192, Palladium 103, Radiopharmaceuticals, Secondary Messengers, Ceramide, Somatomedins, Statins, Steroids, Sulfonyl Thrombin, Thrombin inhibitor, Thrombolytics, Ticlid, Tyrosine kinase, Inhibitors, ST638, AG17, Vasodilator, Histamine, Nitroglycerin, Vitamins E and C, Yeast. Certain embodiments of the present teachings could also be modified so as to deliver one or more alarmin(s) or alarmin activator(s), or a combination of alarmin(s) and alarmin activator(s) to the intracardiac tissue to be treated to accelerate recruitment of endogenous cells, for example, fibroblasts, myocytes, endothelial cells and their progenitors, and progenitor cells of the circulating blood, formation of granulation tissue and re-endothelialization at the site of the intracardiac defect. Exemplary alarmins include members of the family of damage associated molecular pattern molecules (DAMPs) and members of the family of pathogen associated molecular pattern molecules (PAMPs). Exemplary alarmins further include the nuclear protein HMGB1, the S100 family of molecules (cytosolic calcium-binding proteins), heat shock proteins, interleukins (including IL-1a), HDGF (hepatoma-derived growth factor, Gal1 (Galectin 1) and the purinergic metabolites of ATP, AMP, adenosine and uric acid. Alarmin activators include small molecules necessary for maintaining the activity of administered and/or endogenous alarmins. Exemplary alarmin activators include thiol containing reducing agents, including, but not limited to, dithiothreitol, 2-mercaptoethanol, N-7-acetyl-cysteine, sodium sulfite, glutathione, and Probucol, (2,6-ditert-butyl-4-[2-(3,5-ditertbutyl-4-hydroxyphenyl)sulfanylpropan-2-ylsulfanyl]phenol). Exemplary alarmin activators further include non-thiol reducing agents, including, but not limited to, ascorbic acid, sodium hypophosphite, and sodium borohydride.

Now referring to FIGS. 9-12 where the general delivery and deployment steps for the patent ductus arteriosus closure device are disclosed. One skilled in the art should understand that the specific steps of device release should be dictated by the specific embodiments of the device-catheter attachment. Additionally, as used herein, the term "catheter" or "sheath" encompasses any hollow instrument capable of penetrating body tissue or interstitial cavities and providing a conduit for selectively injecting a solution or gas. The term "catheter" or "sheath" is also intended to encompass any elongate body capable of serving as a conduit for one or more of the ablation, expandable or sensing elements. Specifically, in the context of coaxial instruments, the term "catheter" or "sheath" can encompass either the outer catheter body or sheath or other instruments that can be introduced through such a sheath. The use of the term "catheter" should not be construed as meaning only a single instrument but rather is used to encompass both singular and plural instruments, including coaxial, nested, and other tandem arrangements. Moreover, the terms "sheath" or "catheter" are sometime used interchangeably to describe catheters having at least one lumen through which instruments or treatment modalities can pass.

Figure 9:
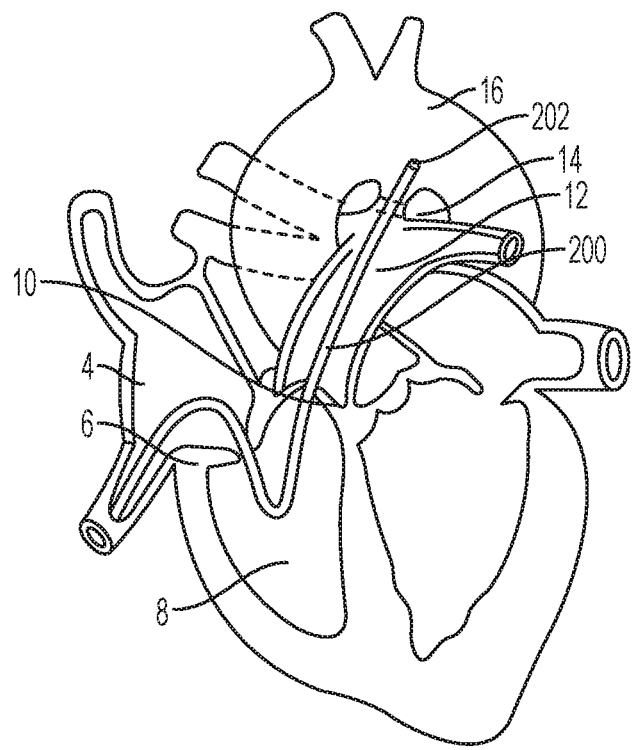
FIGS. 9-12 illustrates an exemplary method of delivering and deploying an exemplary ductus arteriosus closure device across the ductus arteriosus in accordance with the present teachings.

According to some embodiments of the present teaching, the device is delivered percutaneously via a delivery catheter. In various embodiments, a delivery catheter of the present teachings includes a distal end, a proximal end, and a lumen at least extending proximally from the distal end of the delivery catheter. In some embodiments, the lumen extends from the distal end proximally to the proximal end. As shown in FIG. 9, the procedure typically starts with a standard right heart catheterization. In such a procedure, a distal end (202) of the delivery catheter (200) is advanced through the femoral vein, to the inferior vena cava (2) and, to the right atrium (4). The distal end (202) of the delivery catheter (200) then further advances through the tricuspid valve (6) into the right ventricle (8). Upon further advancing through the right ventricle (8), the distal end (202) of the delivery catheter (200) then extends through the pulmonary valve (10) and entering the pulmonary artery (12). Upon further extending distally, the distal end (202) of the device (20) is positioned near the ductus arteriosus (14). FIG. 9 shows that a distal end (202) of a delivery catheter (200) extends across the ductus arteriosus (14) and is positioned inside the descending aorta (16), and the rest portions of the catheter (200) tracing the percutaneous delivery route, with the proximal end of the catheter (not shown) remains outside of the body.

According to some embodiments of the present teachings, a patent ductus arteriosus closure device is extended into an elongated delivery profile where all portions of the device including the distal flange portion, the body portion, the proximal flange portion, and the proximal retrievable portion are collapsed radially and stretched longitudinally so that the device is configured into an elongated tubular like profile orienting longitudinally along the longitudinal axis of the body portion. The device is generally straightened and is suitable for being delivered via a delivery system (not shown). According to some embodiments, the body portion in the delivery configuration also radially collapses and axially elongates compared to that in its deployed configuration. Alternatively, the body portion of the device in the delivery configuration remains generally the same shape and size as that in its deployed configuration. In some embodiments of the present teachings, the device in its delivery configuration is configured to be delivered and deployed through a 3-5 French ID catheter. In some embodiments of the present teachings, the device in its delivery configuration has an overall length of about 5-25 mm, with the length of the body portion being 1-15 mm. In another embodiment, the length of the body portion of a deployed device ranges from about 30-70% of the length of the device in the delivery profile.

According to some embodiments of the present teaching, the patent ductus arteriosus closure device in its delivery profile is preloaded in the distal portion of the delivery catheter and is carried across the ductus arteriosus (14) as the delivery catheter extends percutaneously. In certain embodiments, the patent ductus arteriosus closure device is at least partially positioned in the lumen of the delivery catheter. According to other embodiments, the delivery catheter is positioned across the ductus arteriosus (14) first and the device is then pushed from the proximal end to the distal portion of the delivery catheter.

If the clinician is satisfied with the location, the clinician can start to deploy the device by first deploying the distal flange portion of the device inside the aorta. According to one embodiment, the delivery catheter is retracted proximally to expose the distal flange portion of the device. As the distal flange portion of the device is exposed outside of the delivery catheter, the distal flange portion of the device expands radially and contracts axially to assume its pre-set deployment configuration. In certain embodiments, the distal flange portion of the device expands radially to be substantially perpendicular to the longitudinal axis of the distal section of the body portion.

Figure 10:
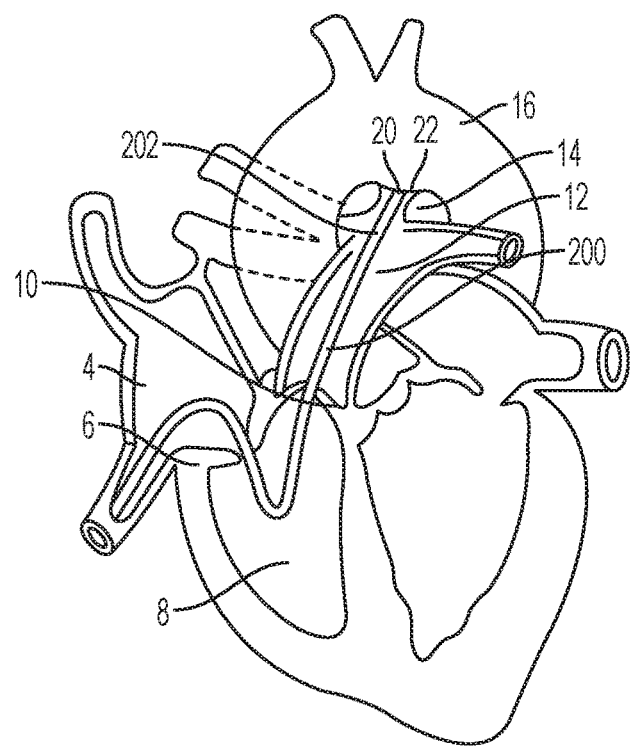

Referring to FIG. 10, the entire delivery assembly, including the delivery catheter (200) and the device (20) with its distal flange portion (22) deployed outside of the delivery catheter (202) and its proximal half still constrained inside the delivery catheter (200), is retracted proximally. As illustrated in FIG. 10, as the delivery catheter (200) still holding the proximal flange portion and body portion of the device (20), the distal flange portion (22) of the device is positioned against the vascular wall inside the aorta (16).

Figure 11:
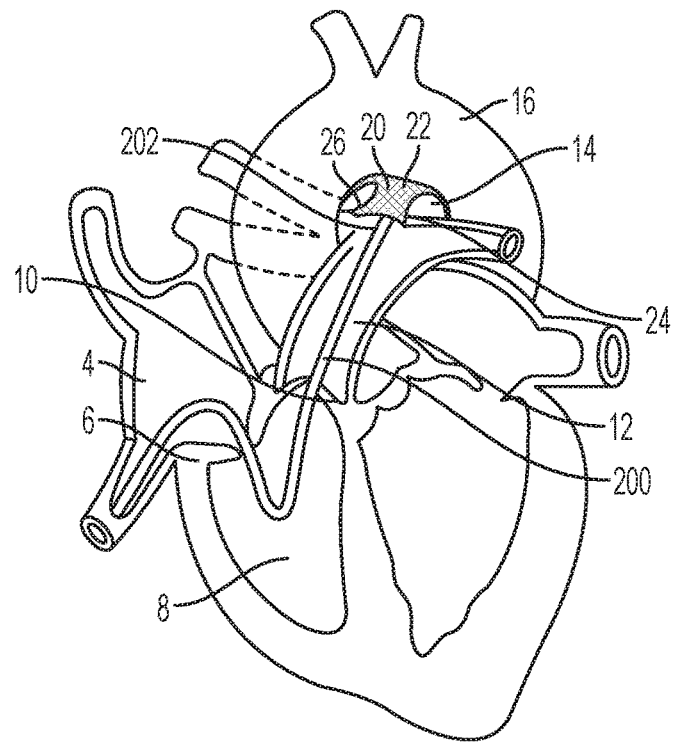

FIG. 11 illustrates an exemplary deployment of the proximal flange portion (24) of the exemplary device (20) using similar steps as described above. According to one embodiment, upon securing the distal flange portion (22) of the device (20) against the vascular wall inside the aorta (16), the delivery catheter (200) is withdrawn proximally to expose the body portion (26) and the proximal flange portion (24) of the device (20) inside the pulmonary artery (12). As the proximal flange portion (24) of the device (20) is exposed, the proximal flange portion (24) of the device (20) expands radially and contracts axially, assuming its pre-set curved deployed configuration. In certain embodiments, the proximal flange portion of the device expands radially to be substantially perpendicular to the longitudinal axis of the proximal section of the body portion.

According to one embodiment of the present teachings, during deployment of the proximal flange portion (24) of the device (20), the proximal retrieval portion (28) of the device (20) remains attaching to the flexible delivery filament/relatively rigid deliver shaft (not shown). According to some embodiments, due to the predetermined length (for example, according to the overall size of the device) of the primary retrieval struts, the proximal flange portion (24) is configured to fully deploy, while the device remains controlled by the clinician. At this point, a clinician could assess the deployment of the device, such as the position of each flange segments and the position of the body portion.

According to one embodiment, if the clinician is not satisfied with the deployment, the clinician retrieves the device. To retrieve the device, a clinician pulls the flexible delivery filament/relatively rigid deliver shaft (not shown) proximally, causing the proximal ends of the primary retrieval struts to slide proximally into the catheter/sheath, straightening the deployed proximal flange portion, and allowing them to enter inside the distal portion of the delivery catheter. As the proximal ends of the primary retrieval portion further slide proximally, the body portion is further straightened and enters into the distal portion of the delivery catheter. When the proximal ends of the primary retrieval portion are continuingly pulled proximally, the distal flange portion is also straightened and enters into the distal portion of the delivery catheter. At this point, the clinician can remove the catheter and the device from the body. Alternatively, the device can be redeployed by following the steps described herein.

Although one retrieval method is described here, one skilled in the art would recognize that other retrieval methods can be incorporated without departing from the scope of the present teachings. For example, while the proximal end of the device is engaged with the delivery assembly, a retrieval means can be advanced to retrieve the device.

Figure 12:
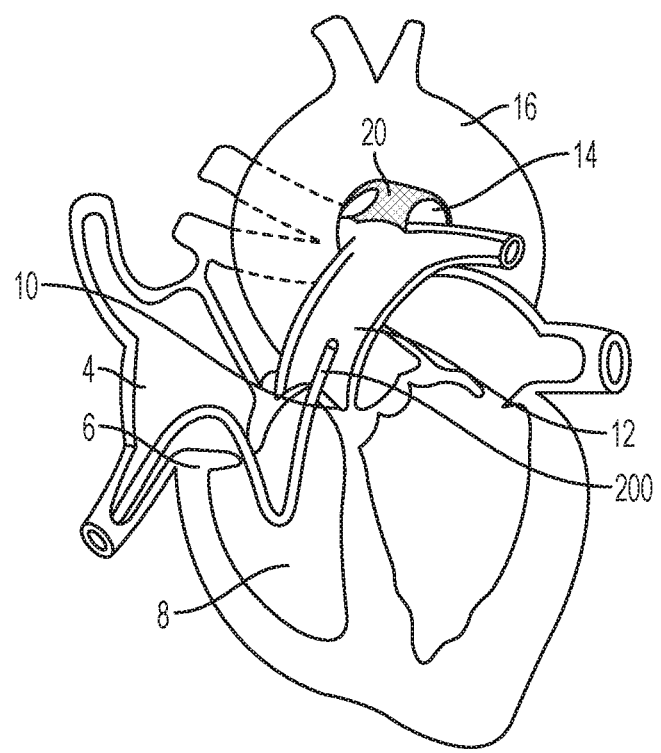

Upon completing deployment of the proximal flange portion of the device, if the clinician is satisfied with the deployment, the device can be completely released. To do so, a clinician releases the attachment mechanisms between the catheter and the proximal retrieval portion (54). As shown in FIG. 12, after the device is completely free of attachment, the delivery catheter and the flexible delivery filament/relatively rigid delivery shaft (not shown) are removed from the patient.

Once deployed, according to some embodiments, all portions of the device are radially expanded and axially shortened. According to some embodiments, as the device expands from its delivery profile, the overall length of the device reduces, sometimes significantly, and the distal flange portion of the device expands, forming a disc-like flange shape; and the proximal flange portion and the proximal retrieval portion of the device proximal to the body portion also expand, forming a disc-like flange shape. According to one embodiment, when deployed in vivo, the radial spans of both the portions that are distal and proximal to the body portion are minimized, sometimes as much as possible, in the device design in order to lower the risk of disc encroachment on the adjacent vascular tissue.

The exemplary techniques for deploying the embodiments described herein are solely for illustration. It should be understood that other techniques can be used instead of, or in combination with, these exemplary techniques, because a clinician can select a technique to deploy an embodiment of the devices described herein based on the particular features of the device, the delivery system, and the anatomy in which the device is being deployed. For example, a clinician might decide to choose foreman artery route to delivery PDA closure device according to some embodiments of the present teaching. To do so, the delivery catheter is delivered through femoral artery to aorta, and further extends through ductus, where the distal end of the delivery catheter is positioned inside the pulmonary artery. From there a clinician starts deployment procedure such as the one described above. In this scenario, the distal flange of the device would positioned against vascular wall inside the pulmonary artery, the proximal flange of the device would positioned against vascular wall inside the aorta, and the body position fixed against ductus tissue.

The methods and devices disclosed herein are useful for closing a patent ductus arteriosus. One skilled in the art would further recognize that devices according to the present teachings could be used to close other parts of the heart and/or vascular portions of the body. For example, the devices disclosed herein can be deployed on the septum between the left and right atria, the left and right ventricles, the left atrium and the coronary sinus, and the like.

Various embodiments have been illustrated and described herein by way of examples, and one of ordinary skill in the art would recognize that variations can be made without departing from the spirit and scope of the present teachings. The present teachings are capable of other embodiments or of being practiced or carried out in various other ways. Also, it is to be understood that the phraseology and terminology employed herein are for the purpose of description and should not be regarded as limiting.

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the patent specification, including definitions, will control. In addition, the materials, methods, and examples are illustrative only and not intended to be limiting.

We claim:

1. A medical device comprising a distal flange portion with a plurality of flange segments having fixed ends and free ends, a proximal flange portion with a plurality of flange segments having fixed ends and free ends, a body portion with a coil section, a non-coiled section, and a tubular lumen extending from the distal flange portion to the proximal flange portion, wherein the fixed ends of the flange segments of the distal and proximal flange portions join the body portion at adjacent ends of the body portion, wherein the device has a deployed configuration with the free ends of the flange segments of the distal and proximal flange portions extending radially outward from the body portion, and a delivery configuration with the free ends of the distal and proximal flange portions collapsing radially inward and aligned with a longitudinal axis of the body portion; and wherein in the deployed configuration, a diameter of the body portion is about 50-70% of an overall diameter of the distal flange portion; the distal flange portion and the proximal flange portion are configured to be positioned against a vascular wall outside two ends of a ductus arteriosus; the body portion is configured to be positioned inside the ductus arteriosus, and the non-coiled section of the body portion is configured to apply a compression force along an outside surface of the body portion toward the surrounding vascular tissues inside the ductus arteriosus, and the coil section of the body portion is configured to adjust the length of the body portion.

2. The device of claim 1, wherein the body portion is adjustable along or perpendicular to a longitudinal axis of the device.

3. The device of claim 1, wherein at least one of the distal and proximal flange portions pivots from the longitudinal axis of the body portion.

4. The device of claim 1, further comprising a proximal retrieval portion connected with the proximal flange portion.

5. The device of claim 4, wherein the proximal retrieval portion comprises at least one retrieval strut.

6. The device of claim 1, wherein the body portion is constructed of a tube with openings.

7. The device of claim 1, wherein the body portion further comprises multiple tabs that bend from a luminal wall of the body portion radially inward to block the tubular lumen when the device is at the deployed configuration.

8. The device of claim 1, wherein the body portion is stretchable.

9. The device of claim 1, wherein the body portion comprises a distal section, a middle section and a proximal section, and the middle section of the body portion is narrower than both the distal section and the proximal section of the body portion.

10. The device of claim 1, wherein the body portion includes a generally funnel shaped distal section, a generally funnel shaped proximal section, and a waist section between the proximal and distal sections.

11. A method of treating a patent ductus arteriosus in a subject in need thereof comprising securing a distal flange portion of a patent ductus arteriosus closure device against the vascular wall inside the descending aorta; wherein the patent ductus arteriosus closure device comprises the distal flange portion with a plurality of flange segments having fixed ends and free ends, a proximal flange portion with a plurality of flange segments having fixed ends and free ends, and a body portion with a coil section, a non-coiled section, and a tubular lumen extending from the distal flange portion to the proximal flange portion, wherein the fixed ends of the flange segments of the distal and proximal flange portions join the body portion at adjacent ends of the body portion; wherein in a deployed configuration, the free ends of the flange segments of the distal and the proximal flange portions extending radially outward from the body portion, are configured to be positioned against a vascular wall outside two ends of a ductus arteriosus, and the body portion is configured to be positioned inside the ductus arteriosus and the non-coiled section of the body portion applies a compression force along an outside surface toward the surrounding vascular tissue inside the ductus arteriosus, and the tubular lumen of the body portion is partially blocked to obstruct a blood flow through the ductus arteriosus, and wherein a diameter of the body portion of the device is about 50-70% of an overall diameter of the distal flange portion.

12. The method of claim 11, wherein the patent ductus arteriosus closure device is preloaded in a delivery catheter, wherein the delivery catheter comprises a distal end, a proximal end, and a lumen extending proximally from the distal end of the delivery catheter.

13. The method of claim 12, comprising advancing the delivery catheter from the pulmonary artery across the ductus arteriosus to the descending aorta, and retracting the delivery catheter proximally to deploy the distal flange portion of the patent ductus arteriosus closure device into the descending aorta, wherein the distal flange portion expands radially.

14. The method of claim 12, comprising retracting the delivery catheter to expose the body portion of the patent ductus arteriosus closure device, wherein the body portion adjusts to the anatomy of the ductus arteriosus independent of the distal flange portion.

15. The method of claim 12, comprising retracting the delivery catheter to expose a proximal flange portion of the patent ductus arteriosus closure device, wherein the proximal flange portion expands radially, wherein the patent ductus arteriosus closure device comprises the proximal flange portion connected proximally with the body portion.

16. The method of claim 15, comprising releasing an attachment mechanism between the delivery catheter and a proximal retrieval portion connected to the proximal flange portion of the ductus arteriosus closure device.

* * * * *